United States Patent
Sakaue

(10) Patent No.: US 8,899,176 B2
(45) Date of Patent: Dec. 2, 2014

(54) ADHESIVE AGENT APPLYING APPARATUS AND ADHESIVE AGENT APPLYING METHOD FOR ABSORBENT ARTICLE

(75) Inventor: Haruhiko Sakaue, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/825,144

(22) PCT Filed: Sep. 14, 2011

(86) PCT No.: PCT/JP2011/070976
§ 371 (c)(1),
(2), (4) Date: Jun. 5, 2013

(87) PCT Pub. No.: WO2012/039333
PCT Pub. Date: Mar. 29, 2012

(65) Prior Publication Data
US 2013/0260031 A1    Oct. 3, 2013

(30) Foreign Application Priority Data

Sep. 22, 2010   (JP) ................................. 2010-212386

(51) Int. Cl.
    *B05C 1/04*    (2006.01)
    (Continued)

(52) U.S. Cl.
    CPC ... *B05D 5/10* (2013.01); *B05C 1/04* (2013.01); *A61F 13/15577* (2013.01);
    (Continued)

(58) Field of Classification Search
    None
    See application file for complete search history.

(56) References Cited

U.S. PATENT DOCUMENTS

| | | | |
|---|---|---|---|
| 4,805,554 A | 2/1989 | McIntyre | |
| 6,242,074 B1 * | 6/2001 | Thomas | 428/137 |
| 2009/0110804 A1 * | 4/2009 | Ogawa et al. | 427/8 |

FOREIGN PATENT DOCUMENTS

| | | |
|---|---|---|
| CN | 1033583 A | 7/1989 |
| JP | S63-296865 | 12/1988 |

(Continued)

OTHER PUBLICATIONS

Chinese First Office Action and English translation from Chinese Application No. 201180045704.5 dated Apr. 30, 2014 (15 pgs).

(Continued)

*Primary Examiner* — Dah-Wei D Yuan
*Assistant Examiner* — Jethro M Pence
(74) *Attorney, Agent, or Firm* — Brinks Gilson & Lione

(57) ABSTRACT

An adhesive agent applying apparatus has an ejecting section that ejects a thermoplastic adhesive agent and applies the thermoplastic adhesive agent onto one surface of a continuous sheet, traveling in a predetermined travel path and relevant to an absorbent article, by ejecting the thermoplastic adhesive agent from the ejecting section. The apparatus includes a contacting-detaching mechanism that causes relative movement between the continuous sheet and the ejecting section along a contacting-detaching direction, an ejecting mechanism that performs an ejecting operation of the thermoplastic adhesive agent from the ejecting section, and a controller that controls the contacting-detaching mechanism and the ejecting mechanism. The controller controls, when a travel speed of the continuous sheet is greater than a predetermined threshold value, the contacting-detaching mechanism and the ejecting mechanism in such a manner that, while causing the ejecting section to be in contact with the one surface of the continuous sheet, the thermoplastic adhesive agent is ejected from the ejecting section, and, when the travel speed is less than or equal to the threshold value, controls the contacting-detaching mechanism and the ejecting mechanism in such a manner that the ejection of the thermoplastic adhesive agent from the ejecting section is stopped and that the continuous sheet and the ejecting section come to a spaced apart state at the time the ejection is stopped or after the ejection has been stopped.

7 Claims, 5 Drawing Sheets

(51) Int. Cl.
*B05C 21/00* (2006.01)
*B05D 5/10* (2006.01)
*A61F 13/15* (2006.01)
*B05C 5/02* (2006.01)
*B05D 1/26* (2006.01)

(52) U.S. Cl.
CPC ......... *A61F 13/15804* (2013.01); *B05C 5/0258* (2013.01); *B05C 21/00* (2013.01); *B05D 1/26* (2013.01); *B05D 2252/02* (2013.01)
USPC ........................................ 118/708; 427/207.1

(56) References Cited

FOREIGN PATENT DOCUMENTS

| | | |
|---|---|---|
| JP | 5-111658 | 5/1993 |
| JP | 05-111658 | 5/1993 |
| JP | 2000-084457 | 3/2000 |
| WO | WO 2010/101284 A1 | 9/2010 |

OTHER PUBLICATIONS

International Search Report from corresponding PCT application No. PCT/JP2011/070976 dated Nov. 15, 2011 (2 pgs).

* cited by examiner

US 8,899,176 B2

ADHESIVE AGENT APPLYING APPARATUS AND ADHESIVE AGENT APPLYING METHOD FOR ABSORBENT ARTICLE

RELATED APPLICATION

The present application is a 35 U.S.C. §371 national stage filing of International Patent Application No. PCT/JP2011/070976, filed Sep. 14, 2011, to which priority is claimed under 35 U.S.C. §120 and through which priority is claimed under 35 U.S.C. §119 to Japanese Priority Patent Application No. 2010-212386, filed Sep. 22, 2010.

TECHNICAL FIELD

The present invention relates to an adhesive agent applying apparatus and an adhesive agent applying method that apply a thermoplastic adhesive agent such as a hot melt adhesive agent onto a continuous sheet such as a nonwoven fabric or a film, and that are used in the manufacture of absorbent articles such as disposable diapers.

BACKGROUND ART

Conventionally, on a production line for disposable diapers and the like, a continuous sheet such as a nonwoven fabric or a film is caused to travel continuously along a predetermined travel path, and, during the travel, a hot melt adhesive agent is applied on one of the surfaces of the continuous sheet.

Such application is performed by a hot melt adhesive agent applying apparatus 20 (hereinafter referred to as an HMA applying apparatus 20) (e.g., see FIG. 1A). The HMA applying apparatus 20 has, for example, a main body which is a head 21 arranged at a predetermined position on a travel path of a continuous sheet 2, and the head 21 has a nozzle 22 serving as an ejecting section and opposing the continuous sheet 2. With the nozzle 22 being in contact with the continuous sheet 2, a hot melt adhesive agent 4 in a molten state is ejected from the nozzle 22 and applied to the continuous sheet 2. It is to be noted that, normally, in order to keep the hot melt adhesive agent 4 in a molten state, the head 21 is heated to, for example, 140° C. to 160° C. with an appropriate heating mechanism, not shown (e.g., see PTL 1).

CITATION LIST

Patent Literature

[PTL 1] JP-A-2000-84457

SUMMARY OF INVENTION

Technical Problem

The production line may be stopped on a regular or irregular basis for various reasons, and in such cases, the travel of the continuous sheet 2 is also stopped. In such a condition where the travel is stopped, if the nozzle 22 of the head 21 is kept in contact with the continuous sheet 2, the continuous sheet 2 will be damaged by heat due to heat input from the head 21 which is at a high temperature as described above. Particularly, in a case where the continuous sheet 2 is a thermoplastic film, since its thickness is small and its heat capacity is low, it will easily melt and break at a contact region.

As an exemplary countermeasure, the above-mentioned heat input can be prevented by spacing the nozzle 22 apart from the continuous sheet 2 when the travel of the continuous sheet 2 is stopped (e.g., see FIG. 1B).

However, in such a case, depending on a relationship between the timing at which ejection of the hot melt adhesive agent 4 is stopped and the timing of detaching, the detaching may provide a disadvantage in that the deposition of the adhesive agent 4 onto the nozzle 22 and its surrounding vicinity portion 22a is promoted, and thus resulting in another problem that the deposited lump may suddenly peel off from the nozzle 22 and get caught in the continuous sheet 2.

More specifically, for example, if the nozzle 22 and the continuous sheet 2 are brought to a spaced-apart state before stopping the ejection of the hot melt adhesive agent 4, the adhesive agent 4 ejected from the nozzle 22 will have nowhere to go (nowhere to be adhered to) and the adhesive agent 4 will deposit on the nozzle 22 and its surrounding vicinity portion 22a. Then, if the lump of the deposited adhesive agent 4 peels off for some reason from the nozzle 22 during the operation of the production line, it will be included in the continuous sheet 2 as a foreign material and may cause other problems such as an increased percentage of rejects.

The present invention has been contrived in view of the above-mentioned drawbacks and its object is to suppress deposition of a thermoplastic adhesive agent on an ejecting section and its surrounding vicinity portion.

Solution to Problem

In order to achieve the above-described advantages, a principal aspect of the invention is an adhesive agent applying apparatus having an ejecting section that ejects a thermoplastic adhesive agent, the adhesive agent applying apparatus applying the thermoplastic adhesive agent onto one surface of a continuous sheet by ejecting the thermoplastic adhesive agent from the ejecting section, the continuous sheet traveling in a predetermined travel path, the continuous sheet being relevant to an absorbent article, the adhesive agent applying apparatus relevant to an absorbent article including:

a contacting-detaching mechanism that causes relative movement between the continuous sheet and the ejecting section along a contacting-detaching direction;

an ejecting mechanism that performs an ejecting operation of the thermoplastic adhesive agent from the ejecting section; and a controller that controls the contacting-detaching mechanism and the ejecting mechanism, the controller controlling, in a case where a travel speed of the continuous sheet is greater than a predetermined threshold value, the contacting-detaching mechanism and the ejecting mechanism in such a manner that, while causing the ejecting section to be in contact with the one surface of the continuous sheet, the thermoplastic adhesive agent is ejected from the ejecting section, and the controller controlling, in a case where the travel speed is less than or equal to the threshold value, the contacting-detaching mechanism and the ejecting mechanism in such a manner that the ejection of the thermoplastic adhesive agent from the ejecting section is stopped and that the continuous sheet and the ejecting section come to a spaced apart state at the time the ejection is stopped or after the ejection has been stopped.

A further aspect of the invention is an adhesive agent applying method of applying a thermoplastic adhesive agent onto one surface of a continuous sheet by ejecting the thermoplastic adhesive agent from an ejecting section, the continuous sheet traveling in a predetermined travel path, the continuous sheet being relevant to an absorbent article, the adhesive agent applying method relevant to an absorbent article including:

in a case where a travel speed of the continuous sheet is greater than a predetermined threshold value, ejecting the thermoplastic adhesive agent from the ejecting section while the ejecting section is being in contact with the one surface of the continuous sheet, and in a case where the travel speed is less than or equal to the threshold value, stopping the ejection of the thermoplastic adhesive agent from the ejecting section and bringing the continuous sheet and the ejecting section to a spaced apart state at the time the ejection is stopped or after the ejection has been stopped.

Features of the invention other than the above will become clear by the description of the present specification and the accompanying drawings.

Advantageous Effects of Invention

According to the present invention, the deposition of a thermoplastic adhesive agent on an ejecting section and its surrounding vicinity portion can be suppressed.

MODE FOR CARRYING OUT THE INVENTION

Figure 1A:
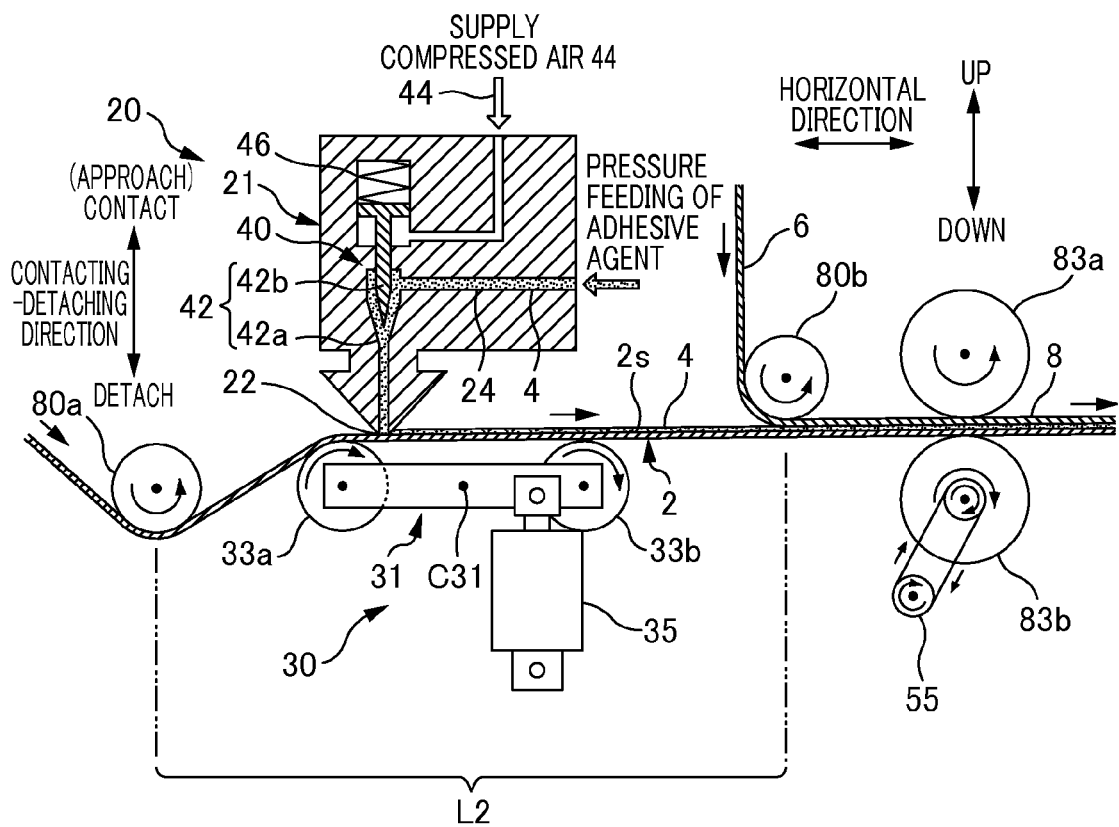
FIG. 1A is a schematic side view illustrating an adhesive agent applying apparatus 20 of a first embodiment in an adhesive agent (adhesive agent 4)-applying state and FIG. 1B is a schematic side view illustrating an application stoppage state of the same.

At least the following matters will be made clear by the description of the present specification with reference to the accompanying drawings.

An adhesive agent applying apparatus having an ejecting section that ejects a thermoplastic adhesive agent is provided in which the adhesive agent applying apparatus applies the thermoplastic adhesive agent onto one surface of a continuous sheet by ejecting the thermoplastic adhesive agent from the ejecting section, the continuous sheet travels in a predetermined travel path, the continuous sheet is relevant to an absorbent article, and in which the adhesive agent applying apparatus relevant to an absorbent article includes:

a contacting-detaching mechanism that causes relative movement between the continuous sheet and the ejecting section along a contacting-detaching direction;

an ejecting mechanism that performs an ejecting operation of the thermoplastic adhesive agent from the ejecting section; and a controller that controls the contacting-detaching mechanism and the ejecting mechanism, the controller controlling, in a case where a travel speed of the continuous sheet is greater than a predetermined threshold value, the contacting-detaching mechanism and the ejecting mechanism in such a manner that, while causing the ejecting section to be in contact with the one surface of the continuous sheet, the thermoplastic adhesive agent is ejected from the ejecting section, and the controller controlling, in a case where the travel speed is less than or equal to the threshold value, the contacting-detaching mechanism and the ejecting mechanism in such a manner that the ejection of the thermoplastic adhesive agent from the ejecting section is stopped and that the continuous sheet and the ejecting section come to a spaced apart state at the time the ejection is stopped or after the ejection has been stopped.

With such adhesive agent applying apparatus relevant to an absorbent article, the continuous sheet and the ejecting section comes to a spaced-apart state at the same time as the stoppage or after the stoppage of ejection of the adhesive agent. Therefore, it is possible to securely avoid a situation where the adhesive agent continues to eject from the ejecting section that is spaced apart from the continuous sheet. Also, since ejection is stopped before coming into the spaced-apart state, the adhesive agent that has been ejected from the ejecting section is generally transferred to the continuous sheet and transported by the sheet. Therefore, the adhesive agent remaining in the ejecting section and its surrounding vicinity portion can be reduced and the deposition of the adhesive agent can be suppressed.

Preferably, in an adhesive agent applying apparatus relevant to an absorbent article described above, in a case where the travel speed is less than or equal to the threshold value, the controller controls the contacting-detaching mechanism and the ejecting mechanism in such a manner that ejection of the thermoplastic adhesive agent from the ejecting section is stopped and that the continuous sheet and the ejecting section come to a spaced apart state after the ejection has been stopped.

With such adhesive agent applying apparatus relevant to an absorbent article, the continuous sheet and the ejecting section comes to a spaced-apart state after the stoppage of ejection of the adhesive agent. Therefore, it is possible to securely avoid a situation where the adhesive agent continues to eject from the ejecting section that is spaced apart from the continuous sheet. Also, since ejection is stopped before coming into the spaced-apart state, the adhesive agent that has been ejected from the ejecting section is generally transferred to the continuous sheet and transported by the sheet. Therefore, the adhesive agent remaining in the ejecting section and its surrounding vicinity portion can be reduced and the deposition of the adhesive agent can be suppressed.

Preferably, in an adhesive agent applying apparatus relevant to an absorbent article described above, the contacting-detaching mechanism is a mechanism that moves the travel path of the continuous sheet in the contacting-detaching direction.

With such adhesive agent applying apparatus relevant to an absorbent article, the ejecting section can be provided so as not to move and fixed at a predetermined position. Therefore, auxiliary equipment such as a supplying mechanism that supplies the thermoplastic agent to the ejecting section need not be configured as a structure that has a movable section that can move relatively in the contacting-detaching direction. Thus, it is not necessary to consider the problem of leakage of adhesive agent from the movable section, which is likely to occur when a movable section is provided, and thus, designing of the apparatus is facilitated.

Preferably, in an adhesive agent applying apparatus relevant to an absorbent article described above, the threshold value is a value greater than zero; and in a case where the travel speed has become less than or equal to the threshold value, the controller controls the ejecting mechanism in such a manner that ejection is stopped before the travel of the continuous sheet is stopped.

With such adhesive agent applying apparatus relevant to an absorbent article, since the travel of the continuous sheet is stopped after the stoppage of ejection, the adhesive agent remaining in the nozzle after the stoppage of ejection will be wiped off by the traveling continuous sheet. As a result, the adhesive agent remaining in the ejecting section and its surrounding vicinity portion can be effectively reduced and deposition of the deposition material can be further suppressed.

Preferably, an adhesive agent applying apparatus relevant to an absorbent article described above further includes:

a heating mechanism that heats the ejecting section, wherein the continuous sheet is a thermoplastic sheet, and the controller controls the contacting-detaching mechanism in such a manner that, before the travel of the continuous sheet is stopped, the continuous sheet and the ejecting section come to a spaced apart state.

With such adhesive agent applying apparatus relevant to an absorbent article, cine the thermoplastic adhesive agent is heated, the adhesive agent can be kept at a high fluidity state and a good ejection capability can be maintained.

Further, since the ejecting section is brought to a spaced-apart state before the stoppage of travel of the continuous sheet, the ejecting section can be prevented from coming into contact with a part of the continuous sheet for a long time. Accordingly, even if the above-mentioned thermoplastic film is utilized as the continuous sheet, it is possible to effectively avoid a situation where a large amount of heat input acts locally on a part of the sheet and causing the corresponding part to melt and break.

Preferably, in an adhesive agent applying apparatus relevant to an absorbent article described above, the threshold value is set at zero.

With such adhesive agent applying apparatus relevant to an absorbent article, the travel of the continuous sheet is stopped before the stoppage of travel. In other words, the travel of the continuous sheet is stopped without waiting for the stoppage of ejection. Accordingly, it is possible to reduce (or substantially to eliminate) a length of a section where the adhesive agent is not applied that may occur at the same time as the stoppage of ejection, and, in other words, a waste length of the continuous sheet can be reduced and a yield of the continuous sheet can be improved.

Further, an adhesive agent applying method of applying a thermoplastic adhesive agent onto one surface of a continuous sheet by ejecting the thermoplastic adhesive agent from an ejecting section is provided in which the continuous sheet travels in a predetermined travel path and the continuous sheet is relevant to an absorbent article, and in which the adhesive agent applying method relevant to an absorbent article includes:

in a case where a travel speed of the continuous sheet is greater than a predetermined threshold value, ejecting the thermoplastic adhesive agent from the ejecting section while the ejecting section is being in contact with the one surface of the continuous sheet, and in a case where the travel speed is less than or equal to the threshold value, stopping the ejection of the thermoplastic adhesive agent from the ejecting section and bringing the continuous sheet and the ejecting section to a spaced apart state at the time the ejection is stopped or after the ejection has been stopped.

With such adhesive agent applying method relevant to an absorbent article, the continuous sheet and the ejecting section comes to a spaced-apart state at the same time as the stoppage or after the stoppage of ejection of the adhesive agent. Therefore, it is possible to securely avoid a situation where the adhesive agent continues to eject from the ejecting section that is spaced apart from the continuous sheet. Also, since ejection is stopped before coming into the spaced-apart state, the adhesive agent that has been ejected from the ejecting section is generally transferred to the continuous sheet and transported by the sheet. Therefore, the adhesive agent remaining in the ejecting section and its surrounding vicinity portion can be reduced and the deposition of the adhesive agent can be suppressed.

First Embodiment

Figure 1B:
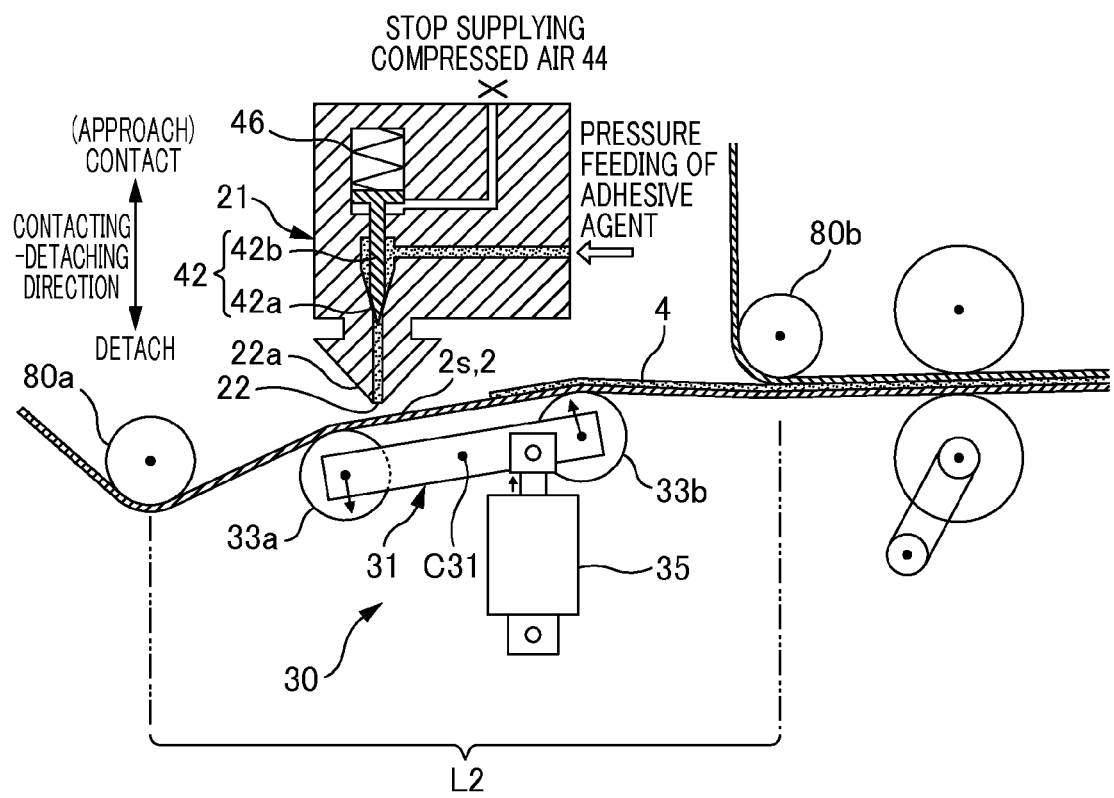

FIGS. 1A and 1B are schematic side views of an adhesive agent applying apparatus 20 of a first embodiment. FIG. 1A shows an adhesive agent (adhesive agent 4)-applying state and FIG. 1B shows an application stoppage state. Also, in FIGS. 1A and 1B, a part of the structure (e.g., a head 21, etc.) is shown in a longitudinal cross-sectional view.

The adhesive agent applying apparatus 20 is used on a production line of absorbent articles such as disposable diapers and sanitary napkins. In other words, as shown in FIG. 1A, the applying apparatus 20 applies the thermoplastic adhesive agent 4 on one surface 2s of a continuous sheet 2 that is traveling, as a component of an absorbent article, along a predetermined travel path on the production line. At a position downstream of the applying apparatus 20 along the travel path, a continuous sheet 6, a single cut sheet and others, that are other components, are superposed and integrally joined as appropriate at portions where the adhesive agent 4 has been applied, and then continuously transported as a semi-finished product 8 of the absorbent article to downstream processes.

The continuous sheet 2 may be, for example, a non-woven fabric, a woven fabric, a film, etc. An exemplary material may be a thermoplastic resin, but it is not limited there to and may also be a pulp fiber.

An exemplary thermoplastic adhesive agent 4 may be hot melt adhesive, but it is not limited thereto. In other words, as long as the adhesive agent 4 has an appropriate thermoplastic property, melts by being heated and can be applied in a fluid state, any adhesive agent other than hot melt adhesive may be used. The following description is based on the assumption that hot melt adhesive is used, and the adhesive agent 4 may be simply referred to as an adhesive agent 4 and the adhesive agent applying apparatus 20 may be is referred to as an HMA applying apparatus 20.

In the following description, a direction of travel of the continuous sheet 2 traveling on a production line is referred to as MD-direction and a width direction of the continuous sheet 2 is referred to as CD-direction. In FIG. 1A, MD-direction is any direction parallel to a plane of paper of FIG. 1A and the MD-direction includes an up-down direction, and the CD-direction is a direction that penetrates through the plane of paper of FIG. 1A.

The HMA applying apparatus 20 includes: the head 21 having a nozzle 22, which serves as an ejecting section of the hot melt adhesive agent 4; a travel path moving mechanism 30, which serves as a contacting-detaching mechanism, that moves a travel path of the continuous sheet 2 in a direction in which one surface 2S of the continuous sheet 2 comes into contact with and detach from the nozzle 22 of the head 21 (corresponds to a thickness direction of the continuous sheet 2 or also corresponds to a direction normal to the one surface 2S of the continuous sheet 2, hereinafter simply referred to as "contacting-detaching direction); an ejecting mechanism 40 that performs an ejecting operation of the adhesive agent 4 from the nozzle 22 of the head 21; and a controller, not shown, that controls the travel path moving mechanism 30 and the ejecting mechanism 40.

Basically, as shown in FIG. 1A, the adhesive agent 4 is applied to the continuous sheet 2 by ejecting the adhesive agent 4 from the nozzle 22 in a state where one surface 2s of the continuous sheet 2 is in contact with the nozzle 22 of the head 21 while the continuous sheet 2 is traveling, and on the other hand, in a case where the adhesive agent 4 is not applied for a long period of time, for example when the travel of the continuous sheet 2 is being stopped, the continuous sheet 2 comes to a state where it is spaced apart from the nozzle 22 of the head 21, as shown in FIG. 1B. Then, because of this spacing, particularly in a case where the continuous sheet 2 is a thermoplastic film, thermal damages such as melting and breaking of the film can be effectively avoided.

In other words, the head 21 is heated to, for example, 140° C. to 160° C., with an appropriate heating mechanism such as an electric heater, which is not shown in the drawings, in order to ensure the fluidity of the adhesive agent 4. Therefore, if the nozzle 22 is in contact with the continuous sheet 2 during the travel stoppage state of the continuous sheet 2, the contacting portion of the continuous sheet 2 will suffer from thermal damages such as melting and breaking due to heat input from the nozzle 22. Concerning this point, with the continuous sheet 2 being spaced apart from the nozzle 22 in the travel stoppage state as described above, the heat input from the nozzle 22 is shut off and the thermal damages of the continuous sheet 2 is avoided.

The spaced apart state shown in FIG. 1B is established after stopping the ejection of the adhesive agent 4. Therefore, it is possible to avoid a situation where the adhesive agent 4 continues to eject from the nozzle 22 that is being spaced apart from the continuous sheet 2, and thus deposition of the adhesive agent 4 onto the nozzle 22 and its surrounding vicinity portion 22a can be suppressed. This will be described later.

Hereinafter, each of the constituent elements 21, 30 and 40, etc., will be described.

As shown In FIG. 1A, the head 21 is fixedly supported at a predetermined position on the travel path of the continuous sheet 2 in an immobilized manner by an appropriate supporting member (not shown) such as a so-called face plate. The nozzle 22 of the head 21 is arranged to oppose one surface 2s of the continuous sheet 2. In this example, the nozzle 22 is configured as a single slit along the CD-direction, but it is not limited thereto and may be of a configuration in which a plurality of holes are arranged along the CD-direction. A flow channel 24 that communicates with the nozzle 22 is provided inside the head 21 and the adhesive agent 4 is delivered to the flow channel 24 with a pump, not shown, which is provided outside. Also, a valve 42 serving as the ejecting mechanism 40 and that opens and closes the flow channel 24 is provided in the flow channel 24. The opening-closing operation of the valve 42 is controlled with the above-mentioned controller and, in an open state of the valve 42 shown in FIG. 1A, the adhesive agent 4 is ejected from the nozzle 22, and in the closed state shown in FIG. 1B, the ejection is stopped.

In detail, with the ejecting mechanism 40 of the illustrated example, the valve 42 includes a valve seat 42a and a valve member 42b having a spool-like shape that comes into contact with and detaches from the valve seat 42a. Compressed air 44 is used as an operating fluid that drives the valve member 42b in a contacting-detaching manner, and it is further configured in such a manner that an on-off operation of the supply of the compressed air 44 is performed by a solenoid valve, not shown. Therefore, as the controller sends an open instruction to the solenoid valve, the solenoid valve supplies the compressed air 44 to the valve 42, as shown in FIG. 1A, and due to the pressure built by the compressed air 44, the valve element 42b is caused to move against a compression spring force of the compression spring member 46 in a direction away from the valve seat 42a, and thus the flow channel 24 opens. On the other hand, as the controller sends a close instruction, the solenoid valve stops supplying the compressed air 44, as shown in FIG. 1B, and the valve element 42b is caused to move in a direction to come into contact with the valve seat 42a due to the compression spring force of the compression spring member 46, and the flow channel 24 closes. However, the configuration of the ejecting mechanism 40 is not limited thereto, and configuration other than this may be used.

As has been described above, the travel path moving mechanism 30 moves along the travel path of the continuous sheet 2 in a thickness direction (contacting-detaching direction) to bring the continuous sheet 2 and the nozzle 22 into a contacting state or into a spaced-apart state. In this example, a seesaw structure is utilized. In other words, as shown in FIG. 1A, the mechanism 30 includes a seesaw member 31 supported in a swingable and rotatable manner about an axis of rotation C31 extending in the CD-direction and an air cylinder 35 serving as a driving source that swingably drives the seesaw member 31, and further, rollers 33a and 33b are provided on either swing ends of the seesaw member 31 in a rotatable manner about axes of rotation extending in the CD-direction. The continuous sheet 2 is provided along a peripheral surface of each of the rollers 33a and 33b in such a manner that the continuous sheet 2 does not come off from the peripheral surface.

Accordingly, as the seesaw member 31 tips from a substantially horizontal position (a position shown in FIG. 1A) where the continuous sheet 2 is in contact with the nozzle 22 of the head 21 in such a manner that the roller 33a proximate to the nozzle 22 moves in a direction away from the nozzle 22, the continuous sheet 2 will come to a state where it is spaced apart from the nozzle 22 as shown in FIG. 1B. Also, with an opposite operation, the continuous sheet 2 will come back to a state where it is in contact with the nozzle 22.

Further, the mechanism 30 has the seesaw member 31 as its main body. Therefore, a change in a tension of the continuous sheet 2 which may arise when switching from the above-mentioned contacting state to a spaced apart state can be effectively suppressed, and as a result, a meandering problem of the continuous sheet 2 due to the change in tension can be effectively avoided.

In detail, first, when changing over from the contacting state to the spaced-apart state as described above, the pair of rollers 33a and 33b move in such a manner that the roller 33b farther from the nozzle 22 (hereinafter referred to as a second roller 33b) moves generally in a direction opposite to the roller 33a nearer to the nozzle 22 (hereinafter referred to as a first roller 33a) in the contacting-detaching direction by an amount of displacement of the roller 33a in the contacting-detaching direction (In FIG. 1A, an up-down direction). Therefore, a path length L2 of the continuous sheet 2 across a pair of pass line rollers 80a, 80b that are adjacent to and directly downstream and upstream of the seesaw member 31 along the travel path does not depend on the changing over from the contacting state shown in FIG. 1A to the spaced-apart state shown in FIG. 1B, and is kept in a generally constant length. As a result, the variation of tension in the continuous sheet 2 due to the switching over from the contacting state to the spaced apart state can be generally suppressed.

It has been described in the description above that the continuous sheet 2 is provided across the first roller 33a and the second roller 33b in such a manner that the continuous sheet 2 is kept so as not to come off from the peripheral surface of each of the rollers 33a and 33b even if the seesaw member 31 swings, and this is achieved by adjusting positions of the pair of pass line rollers 80a and 80b arranged adjacent to and downstream and upstream of the seesaw member 31. In other words, each of the pair of pass line rollers 80a and 80b is a fixed roller that is provided in a rotatable manner about an axis along the CD-direction and that is immovably fixed at a predetermined position, and each of the pass line rollers 80a and 80b is arranged to come into contact with one of the surfaces of the continuous sheet 2, which surface 2s being opposite to the surface in contact with the first roller 33a and the second roller 33b. The pass line roller 80a nearer to the first roller 33a is arranged in such a manner that the continuous sheet 2 is provided in a substantially S-shape between the pass line roller 80a and the first roller 33a, and further, the pass line roller 80b nearer to the second roller 33b is arranged in such a manner that the continuous sheet 2 is provided in a substantially S-shape between the pass line roller 80b and the second roller 33b. Thus, the continuous sheet 2 does not depend on the swinging of the seesaw member 31 and does not come off from the peripheral surface of the first roller 33a and the peripheral surface of the second roller 33b.

The controller is, for example, a computer or a PLC (programmable logic controller) and has a processor and a memory. The processor reads out and executes an appropriate program stored in the memory and sends various instructions to the travel path moving mechanism 30 and the ejecting mechanism 40 to control operations of these mechanisms 30 and 40.

It is to be noted that a measurement value of travel speed of the continuous sheet 2 is utilized in such control, and a signal representing the measurement value of travel speed is inputted into the controller on a real-time basis from a rotary encoder 55 provided on a roller that rotates in synchronization with the continuous sheet 2. The roller on which the encoder 55 is attached may be, for example, one of a pair of pressing rolls 83a and 83b that is located downstream of the pass line roller 80a and the pass line roller 80b, and presses the continuous sheet 2, and in the illustrated example, the encoder 55 is provided on the pressing roll 83b, but it is not limited thereto.

Now, referring to a flowchart of FIG. 2, an operation of the HMA applying apparatus 20 associated with travel stoppage of the continuous sheet 2 will be described.

First, as has been described above, the signal of the measurement value of travel speed of the continuous sheet 2 is inputted on a real-time basis to the controller of the HMA applying apparatus 20 and the controller always compares whether the measurement value of travel speed is less than or equal to a threshold value that is prestored in the memory.

During a steady production shown in FIG. 1A, since the travel speed is generally greater than the above-mentioned threshold value, the controller determines that the measurement value of travel speed is greater than the threshold value, and thus the controller sends an open instruction to the ejecting mechanism 40 and sends a contact instruction to the travel path moving mechanism 30. Accordingly, the ejecting mechanism 40 opens the valve 42 and ejects the adhesive agent 4, and the travel path moving mechanism 30 causes the continuous sheet 2 and the nozzle 22 to come into the contacting state.

On the other hand, in order to stop the travel of the continuous sheet 2, when a speed of the continuous sheet 2 is reduced by a control of an appropriate integrated controller, the measurement value of the travel speed will gradually decrease and eventually becomes less than or equal to the threshold value. Then, the controller determines that the measurement value has become less than or equal to the threshold value (S10), sends a close instruction to the ejecting mechanism 40 (S12), and thus the ejecting mechanism 40 closes the valve 42 and stops the ejection of the adhesive agent 4 (see FIG. 1B).

Simultaneously with the sending of the close instruction to the ejecting mechanism 40, the controller sends a detach instruction to the travel path moving mechanism 30 (S14). Then, the air cylinder 35 of the travel path moving mechanism 30 moves the seesaw member 31 to tip about the axis of rotation C31 to switch over the continuous sheet 2 that is in contact with the nozzle 22 to a state where the continuous sheet 2 is spaced apart from the nozzle 22. In other words, simultaneously with the ejection stoppage of the adhesive agent 4 from the nozzle 22, the continuous sheet 2 comes to a state where it is spaced apart from the nozzle 22.

Therefore, it is possible to securely avoid a situation where the adhesive agent 4 continues to eject from the nozzle 22 that is spaced apart from the continuous sheet 2. Also, since ejection is stopped at the same time as coming into the spaced apart state, the adhesive agent 4 that has been ejected from the nozzle 22 is generally transferred to the continuous sheet 2 and transported by the sheet 2. Therefore, the adhesive agent 4 remaining in the nozzle 22 and its surrounding vicinity portion 22a can be reduced and deposition of the adhesive agent 4 can be suppressed.

It is to be noted that the above-mentioned "ejection stoppage" is, for example, a state where the close operation of the valve 42 has been completed and "spaced apart state" is a state where the detaching operation has been completed. Therefore, to be exact, a situation where the "ejection stoppage" and "to come to the spaced apart state" are performed at the same time in accordance with a flowchart of FIG. 2 is a case where an operation time period T42 of the valve 42 and an operation time period T31 of the seesaw member 31 have mutually the same value. That is to say, such situation is established when the operation time period T42, from the sending of the close instruction to the completion of the closing operation of the valve 42, and the operation time period T31, from the sending of the detach instruction to the completion of the detaching operation have mutually the same value. Regarding this point, in practice, there are many cases where the operation time period T42 and the operation time period T31 are different from each other. In such a case, a timing of ejection stoppage and a timing of coming to a spaced apart state can be synchronized by delaying the sending of one of the close instruction and the detach instruction that has a shorter operation time period by a deviation between the operation time period T42 and the operation time period T31.

Further, in a case where a speed value greater than zero is set as the above-mentioned threshold value of the travel speed, if a large value Vth is set as the speed value, the travel of the continuous sheet 2 can be stopped after the ejection stoppage and the detaching. In other words, the nozzle 22 can be brought to the spaced apart state before stopping the travel of the continuous sheet 2. Therefore, it is possible to prevent the nozzle 22 from being in contact with a part of the continuous sheet 2 for a long time. Accordingly, even if the above-mentioned thermoplastic film is utilized as the continuous sheet 2, it is possible to effectively avoid a situation where a large amount of heat input acts locally on a part of the film and the corresponding part melts and breaks.

The large value Vth concerning the above-mentioned speed value is, for example, such a speed value that a time required for the travel speed to decrease from Vth to zero is longer than the longer one of the above-mentioned operation time period T42 and the operation time period T31. Such speed value Vth can be determined by actually measuring a relationship between each value of the travel speed during reduction of the speed and the time taken from each value to the stoppage of travel.

On the other hand, if zero is set as the above-mentioned threshold value of the travel speed, the ejection stoppage and the detaching will be performed after the travel of the continuous sheet 2 has been stopped. Therefore, the travel of the continuous sheet 2 is stopped without waiting for the ejection stoppage or the detaching operation. Accordingly, a length of a portion where the adhesive agent 4 is not applied, which may be produced in association with the stoppage of ejection and the detaching, can be reduced (or substantially eliminated). In other words, a waste length of the continuous sheet 2 can be reduced and a yield of the continuous sheet 2 can be improved. However, in this case, since there is a possibility that the nozzle 22 is kept in contact with a part of the continuous sheet 2 for a long time, such a setting is limited to a case where the continuous sheet 2 is a sheet of, for example, a nonwoven fabric which shows a certain resistance against heat.

Figure 3:
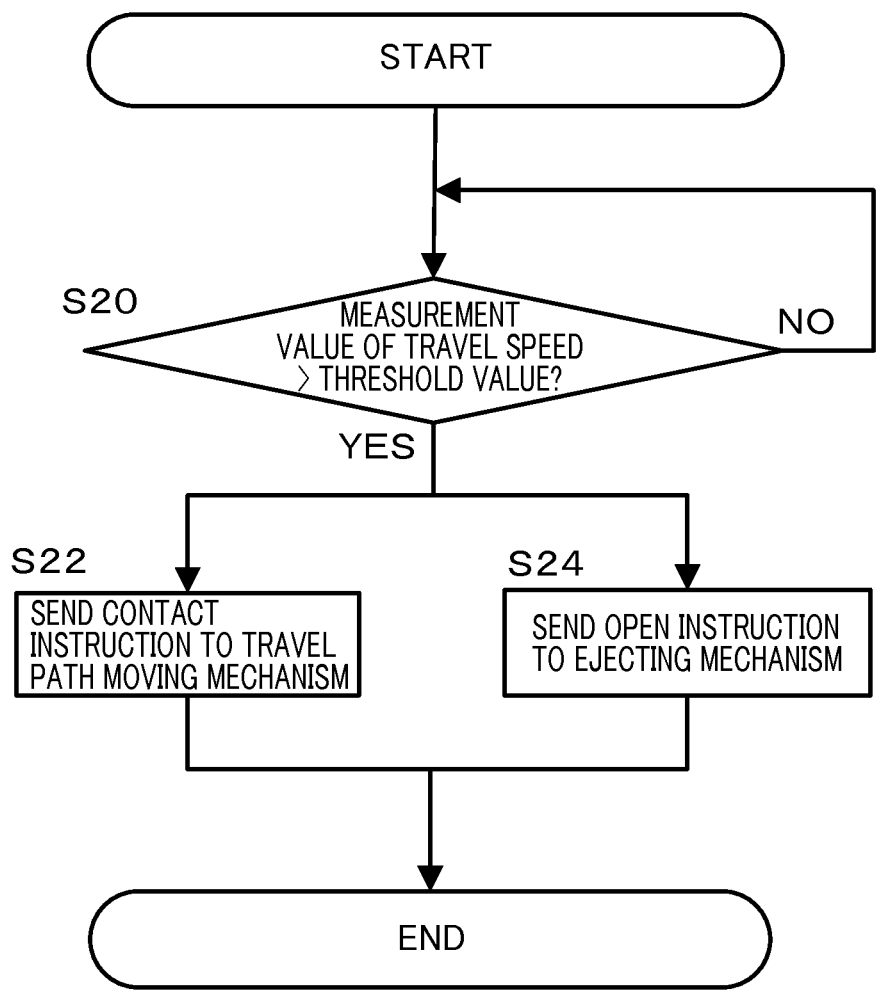
FIG. 3 is a flowchart of an operation of an HMA applying apparatus 20 when restarting the traveling of the continuous sheet 2.

When starting the travel of the continuous sheet 2 again, the controller controls the ejecting mechanism 40 and the travel path moving mechanism 30 in accordance with a flowchart of FIG. 3.

In detail, first, in order to start the travel of the continuous sheet 2 again, the continuous sheet 2 is accelerated by being controlled by the above-mentioned integrated controller. Accordingly, the measurement value of travel speed also becomes gradually greater and eventually exceeds the threshold value.

Then, the controller of the HMA applying apparatus 20 determines that the measurement value of travel speed is greater than the threshold value (S20). Thus the controller sends the contact instruction to the travel path moving mechanism 30 (S22) and sends the open instruction to the ejecting mechanism 40 (S24). Then, the travel path moving mechanism 30 brings the continuous sheet 2 and the nozzle 22 into a contacting state and the ejecting mechanism 40 opens the valve 42 to eject the adhesive agent 4 from the nozzle 22. Thus, the HMA applying apparatus 20 comes to a steady production state.

Figure 4:
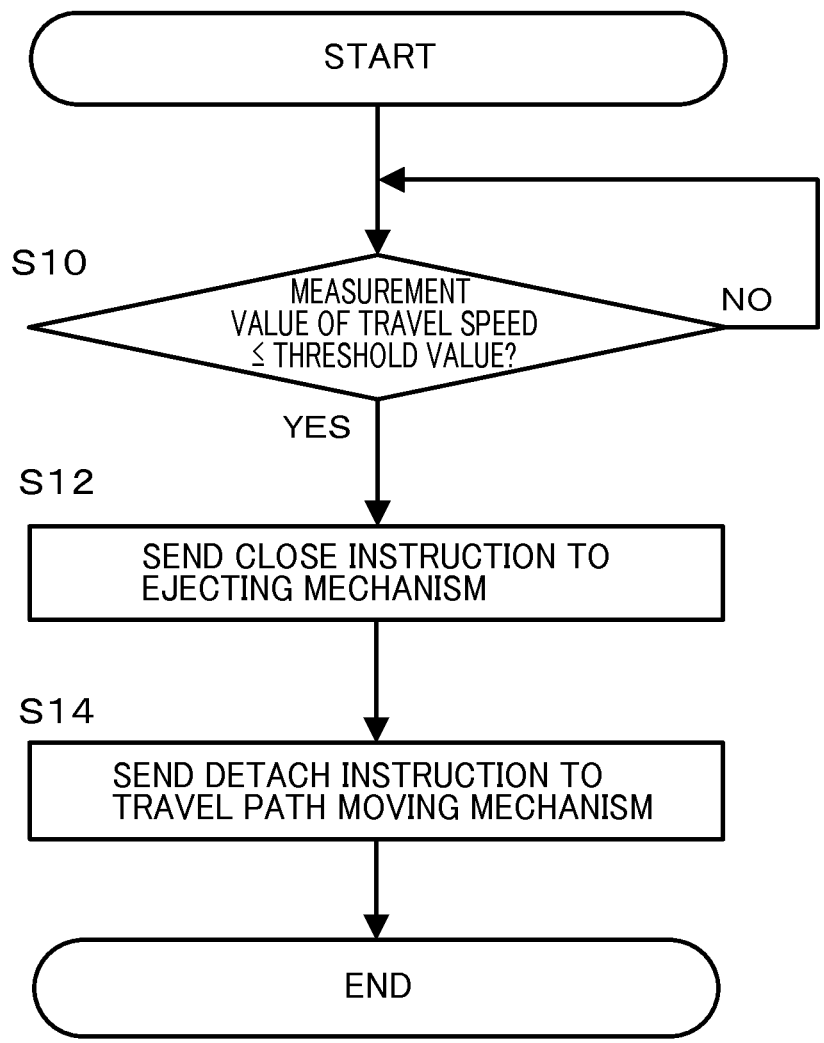
FIG. 4 is a variant of a flowchart of an operation of an HMA applying apparatus 20 associated with the stoppage of the traveling of the continuous sheet 2.

FIG. 4 is a variant of a flowchart of an operation of an HMA applying apparatus 20 associated with the travel stoppage of the continuous sheet 2.

Figure 2:
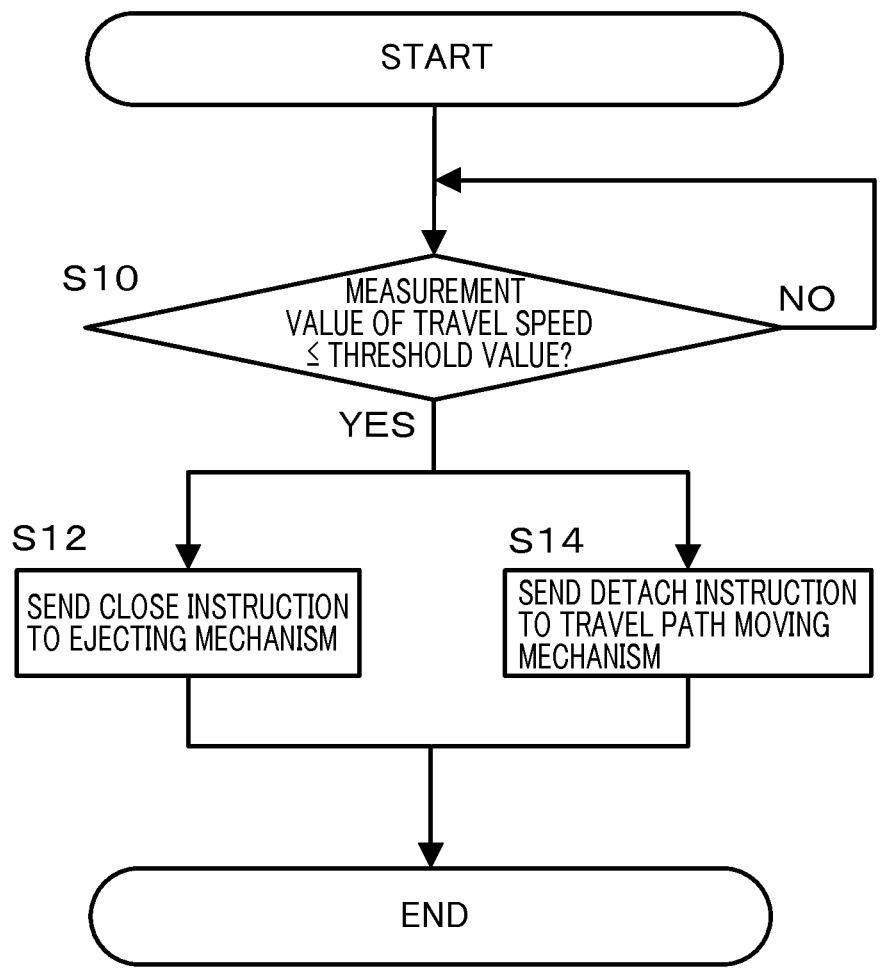
FIG. 2 is a flowchart of an operation of an HMA applying apparatus 20 associated with stoppage of the traveling of the continuous sheet 2.

In the above-mentioned flowchart shown in FIG. 2, it is brought to the spaced apart state at the same time as the ejection stoppage, whereas the present variant is configured such that it is brought to the spaced apart state after the ejection stoppage.

In detail, first, in order to stop the travel of the continuous sheet 2, the speed of the continuous sheet 2 is reduced by an appropriate control by the integrated controller.

Also, as has been described above, the signal of the measurement value of travel speed of the continuous sheet 2 is inputted to the controller of the HMA applying apparatus 20 on a real-time basis, and the controller always compares the measurement value of travel speed with the threshold value prestored in the memory.

In association with the above-mentioned reduction of speed, in a case where the controller determines that the measurement value is less than or equal to the threshold value, i.e., when it has become less than or equal to the threshold value, the controller sends the close instruction to the ejecting mechanism 40 (S12). Then, the ejecting mechanism 40 stops the ejection of the adhesive agent 4 by closing the valve 42.

After sending of the close instruction, i.e., after a predetermined delay time period Td has elapsed from the sending, the controller sends the detach instruction to the travel path moving mechanism 30 (S14). Then, the air cylinder 35 of the travel path moving mechanism 30 moves the seesaw member 31 to tip about the axis of rotation C31 and thus the continuous sheet 2 is switched over from a state where it is in contact with the nozzle 22 a state where it is spaced apart from the nozzle 22. It is to be noted that, here, in a case where the above-mentioned operation time periods T42 and T31 are different from each other, the delay time period Td may be set at a value greater than a value obtained by subtracting the operation time period T31 from the operation time period T42 (=T42−T31), so that the detaching operation will be made to complete after the completion of the closing operation of the valve 42, i.e., ejection stoppage.

In this manner, by bringing the continuous sheet 2 and the nozzle 22 to a spaced apart state after the ejection stoppage, an effect described below can be achieved. First, it is possible to securely avoid a situation in which the adhesive agent 4 continues to eject from the nozzle 22 spaced part from the continuous sheet 2. Also, since it comes to a spaced-apart state after the ejection has been stopped, the adhesive agent 4 that has been ejected from the nozzle 22 will be transferred to the continuous sheet 2 and transported by the sheet 2. Therefore, the adhesive agent 4 remaining in the nozzle 22 and its surrounding vicinity portion 22a can be reduced and deposition of the adhesive agent 4 can be suppressed.

Also, in a case where a speed value greater than zero is set as the above-mentioned threshold value for the travel speed, when a large value Vth is set as the speed value, the travel of the continuous sheet 2 can be stopped after the ejection stoppage. Therefore, the adhesive agent 4 remaining in the nozzle 22 after the ejection stoppage will be wiped off by the traveling continuous sheet 2. In other words, after the ejection stoppage, a long length of the continuous sheet 2 in the travel direction in contact with the nozzle 22 can be ensured, and thus a length of the continuous sheet 2 for wiping the adhesive agent 4 remaining in the nozzle 22 (wiping length) can be increased. As a result, the adhesive agent 4 remaining in the nozzle 22 and its surrounding vicinity portion 22a can be effectively reduced and deposition of the adhesive agent 4 can be further suppressed.

It is to be noted that the large value Vth concerning the above-mentioned speed value is, for example, such a speed value that a time required for the travel speed to decrease from Vth to zero is longer than the longer the above-mentioned operation time period T42. Such speed value Vth can be determined by actually measuring a relationship between each value of the travel speed during reduction of the speed and the time taken from each value to the stoppage of travel.

Further, depending on the setting of the above-mentioned delay time period Td that is a time period between the sending of the close instruction (S12) and the sending of the detach instruction (S14), the continuous sheet 2 and the nozzle 22 may be adjusted to come to a spaced apart state before stopping the travel of the continuous sheet 2. By adjusting in such a manner, since the nozzle 22 is spaced apart before stopping the travel of the continuous sheet 2, the nozzle 22 can be prevented from coming into contact with a part of the continuous sheet 2 for a long time. Accordingly, even if the above-mentioned thermoplastic film is utilized as the continuous sheet 2, it is possible to effectively avoid a situation where a large amount of heat input acts locally on a part of the film and causing the corresponding part to melt and break.

On the other hand, if zero is set as the above-mentioned threshold value, the ejection stoppage and the detaching will be performed after the travel of the continuous sheet 2 has been stopped. Therefore, the travel of the continuous sheet 2 is stopped without waiting for the ejection stoppage or the detaching operation. Accordingly, a length of a portion where the adhesive agent 4 is not applied, which may be produced in association with the stoppage of ejection, can be reduced (or substantially eliminated). In other words, a waste length of the continuous sheet 2 can be reduced and a yield of the continuous sheet 2 can be improved. However, in this case, since there is a possibility that the nozzle 22 is kept in contact with a part of the continuous sheet 2 for a long time, such a setting is limited to a case where the continuous sheet 2 is a sheet of, for example, a nonwoven fabric which shows a certain resistance against heat.

Second Embodiment

Figure 5A:
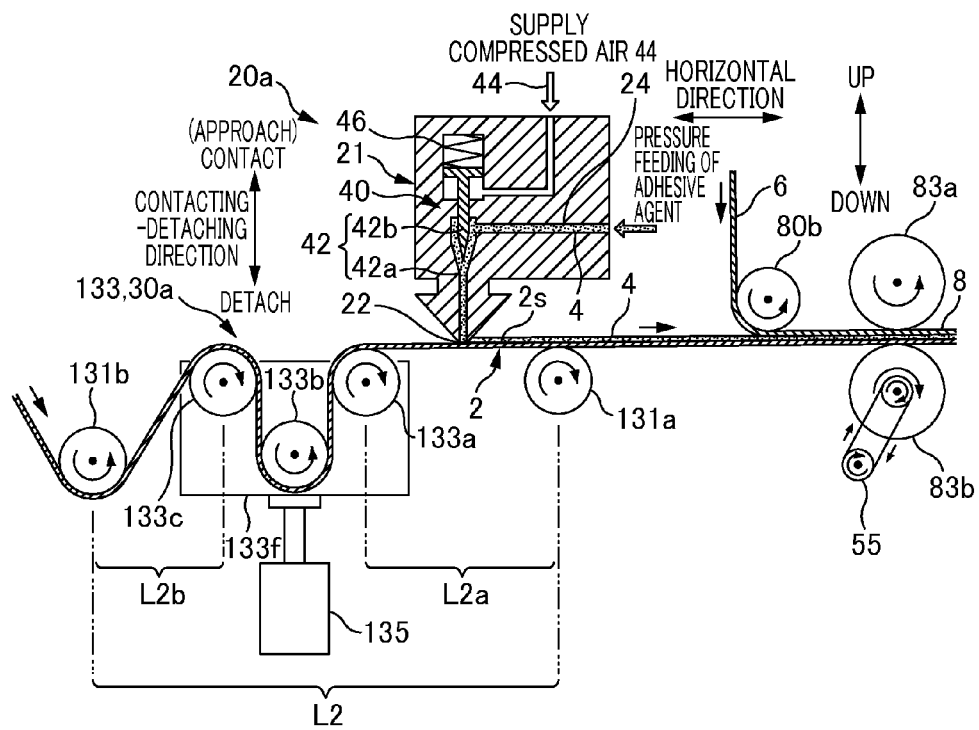
FIG. 5A is a schematic side view illustrating an adhesive agent applying apparatus 20a of a second embodiment in an adhesive agent (adhesive agent 4)-applying state and FIG. 5B is a schematic side view illustrating an application stoppage state of the same.
Figure 5B:
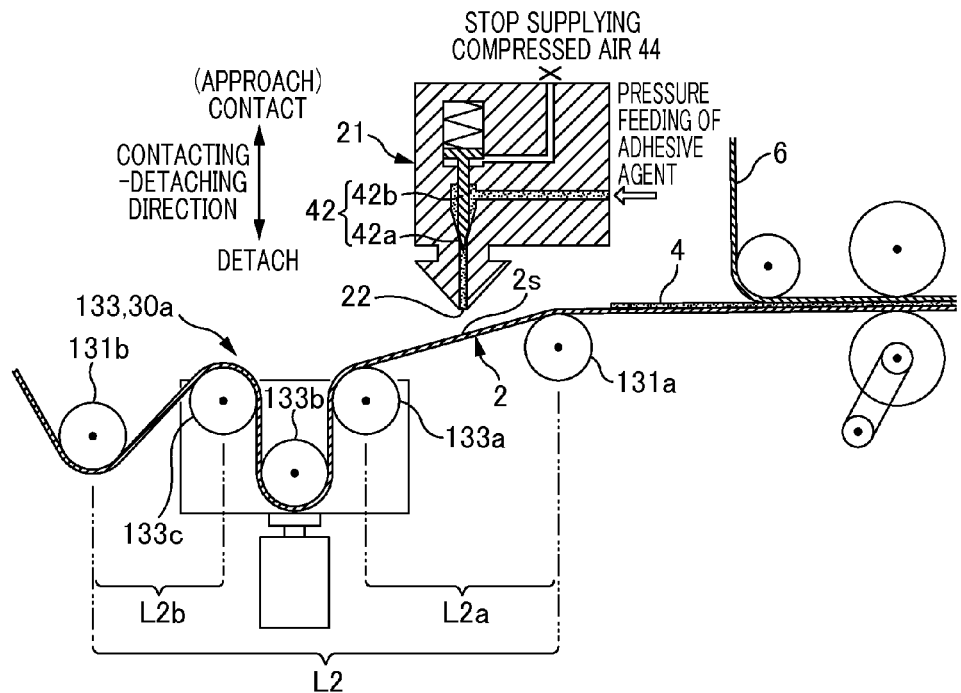

FIGS. 5A and 5B are schematic side views illustrating an HMA applying apparatus 20a of the second embodiment. FIG. 5A shows an adhesive agent (adhesive agent 4)-applying state and FIG. 5B shows an application stoppage state. Also, in FIGS. 5A and 5B, a part of the structure (e.g., the head 21, etc.) is illustrated in a longitudinal cross-sectional view.

As can be elucidated by referring to FIGS. 5A and 5B, the difference from the first embodiment resides in the configuration of a travel path moving mechanism 30a. Therefore, the following description is mainly directed to the travel path moving mechanism 30a. Other identical structures will be indicated with the same reference numerals and explanations thereof will be omitted.

As shown in FIG. 5A, the travel path moving mechanism 30a is arranged in such a manner that one surface 2s of the continuous sheet 2, which is passed across the mechanism 30a, opposes the nozzle 22 of the head 21. The mechanism 30a includes a pair of pass line rollers 131a, 131b across which the continuous sheet 2 is passed; a group of rollers 133 arranged at a position between these pass line rollers 131a, 131b and guided in a reciprocable manner along the contacting-detaching direction; and an air cylinder 135 that serves as a driving source that moves the group of rollers 133 in a reciprocable manner in the contacting-detaching direction.

The pass line rollers 131a, 131b are fixed rollers that are rotatable about respective axes lying along the CD-direction and immovably fixed at predetermined positions. Regarding the pair of pass line rollers 131a, 131b, the roller 131a nearer to the nozzle 22 in the travel direction is also nearer to the nozzle 22 in the contacting-detaching direction. Hereinafter, the pass line roller 131a nearer to the nozzle 22 is referred to as a first pass line roller 131a and the farther pass line roller 131b is referred to as a second pass line roller 131b.

The group of rollers 133 includes an odd number of, for example, three or more (in the illustrated example, three) rollers 133a, 133b, 133c, and the continuous sheet 2 is passed across these rollers 133a, 133b, 133c in a hairpin manner (in the illustrated example, in a U-shaped manner) along the contacting-detaching direction. Further, these rollers 133a, 133b, 133c are supported with an appropriate frame member 133f and thus these rollers 133a, 133b, 133c are configured to be movable in a reciprocable manner in the contacting-detaching direction with a relative positional relationship between each other being maintained. Further, the nozzle 22 of the head 21 is arranged between the group of rollers 133 and the first pass line roller 131a, which is the pass line roller 131a nearer to the nozzle 22.

Accordingly, defining a reference position as a position of the group of rollers 133 at which the continuous sheet 2 comes into contact with the nozzle 22 (see the state shown in FIG. 5A), with the group of rollers 13 being moved from this reference position and away from the nozzle 22 along the contacting-detaching direction, the continuous sheet 2 will come to a state where it is spaced apart from the nozzle 22 (see the state shown in FIG. 5B). Also, with an opposite operation, the sheet 2 can be brought back to a state where it is in contact with the nozzle 22.

This travel path moving mechanism 30a of the second embodiment is also elaborated in that a variation of tension in the continuous sheet 2 when switching between the contacting state and the spaced apart state is suppressed. Explaining about the elaboration, first, among the rollers 133a, 133b, 133c of the group of rollers 133, concerning the contacting-detaching direction, the roller 133a adjacent to the first pass line roller 131a is located at the same position as the first pass line roller 131a or at a position farther than this from the nozzle 22. Among the rollers 133a, 133b, 133c of the group of rollers 133, concerning the contacting-detaching direction, the roller 133c adjacent to the second pass line roller 131b is located at a position nearer to the nozzle 22 than the second pass line roller 131b.

Therefore, even if the group of rollers 133 moves in the contacting-detaching direction, the path length L2 of the continuous sheet 2 between the first pass line roller 133a and the second pass line roller 131b is kept at a generally constant length. In other words, in a case where the group of rollers 133 has moved from the position nearer to the nozzle 22 as shown in FIG. 5A to a position farther from the nozzle 22 along the contacting-detaching direction as shown in FIG. 5B, a path length L2a of the continuous sheet 2 between the first pass line roller 131a and the roller 133a of the group of rollers 133 becomes longer, whereas a path length L2b of the continuous sheet 2 between the second pass line roller 131b and the roller 133c of the group of rollers 133 becomes shorter. Therefore, the path length L2 of the continuous sheet 2 between the first pass line roller 131a and the second pass line roller 131b is kept at a generally constant length. As a result, a variation of tension in the continuous sheet 2 when switching between the contacting state and the spaced apart state is generally suppressed, and as a result, a meandering problem of the continuous sheet 2 due to the variation of tension can be effectively avoided.

It is to be noted that the travel stoppage and travel restart operations of the HMA applying apparatus 20a using such travel path moving mechanism 30a is generally similar to those explained in the first embodiment, and thus the explanation thereof will be omitted.

OTHER EMBODIMENT

Although the embodiments of the present invention have been described above, the present invention is not limited to such embodiments, and variants described below are also possible.

In the aforementioned embodiments, it has been described that the absorbent article may be a disposable diaper or a sanitary napkin, but it is not limited thereto as long as it absorbs liquid excretion such as urine or menstrual blood, and may also be, for example, a pet sheet that absorbs liquid excretion from pet animals.

In the aforementioned embodiments, the nozzle 22 serving as the ejecting section and in contact with the continuous sheet 2 at the tip of the nozzle 22 is shown by way of example, but it is not limited thereto. In other words, the adhesive agent ejected from the nozzle 22 may be applied to the continuous sheet 2 in such a manner that a member provided at the tip of the nozzle 22 may serve as the ejecting section and come into contact with the continuous sheet 2. One of the examples is a configuration in which a rotatable spherical body such as a ball of a ball-pointed pen is provided at the tip of the nozzle 22 and the spherical body moves around due to contact with the continuous sheet 2.

In the aforementioned embodiments, the travel path moving mechanisms 30, 30a that moves the travel path of the continuous sheet 2 have been shown as an exemplary contacting-detaching mechanism, but it is not limited thereto. For example, contrary to the above-mentioned embodiments, with a configuration in which the travel path of the continuous sheet 2 in the above-mentioned contacting-detaching direction is switched and the head 21 is reciprocable in the contacting-detaching direction, the contacting state and the spaced apart state may be switched by moving the head 21 towards and away from the continuous sheet 2 in the contacting-detaching direction. In such a case, the contacting-detaching mechanism includes an appropriate guide member such as a linear guide that guides the head 21 in a reciprocable manner in the contacting-detaching direction and a driving source such as an air cylinder or a hydraulic cylinder that reciprocates the head 21 in the contacting-detaching direction.

In the aforementioned embodiments, although the air cylinder 35, 135 is used as the driving source of the travel path moving mechanism 30, 30a, it is not limited thereto, as long as the driving source can move the seesaw member 31 or the group of rollers 133. For example, a hydraulic cylinder or an electric motor may be used.

In the aforementioned embodiments, the travel path of the continuous sheet 2 when in contact with the nozzle 22 is substantially horizontal, but it is not limited there to, and the travel path may extend along a vertical direction or may be inclined at any angle between horizontal and vertical.

REFERENCE SIGNS LIST 2 continuous sheet, 2s one surface, 4 thermoplastic adhesive,
6 continuous sheet, 8 semifinished product,
20 adhesive agent applying apparatus, 20a adhesive agent applying apparatus,
21 head, 22 nozzle (ejecting section),
22a surrounding vicinity portion,
24 flow channel,
30 travel path moving mechanism (contacting-detaching mechanism),
30a travel path moving mechanism (contacting-detaching mechanism),
31 seesaw member, 33a first roller, 33b second roller,
35 air cylinder, 40 ejecting mechanism, 42 valve,
42a valve seat, 42b valve element, 44 compressed air,
46 compression spring member, 55 rotary encoder,
80a pass line roller, 80b pass line roller,
83a press roll, 83b press roll,
131a first pass line roller, 131b second pass line roller,
133 group of rollers, 133a roller, 133c roller,
133f frame member, 135 air cylinder,
C31 axis of rotation

The invention claimed is:

1. An adhesive agent applying apparatus having an ejecting section that ejects a thermoplastic adhesive agent, the adhesive agent applying apparatus applying the thermoplastic adhesive agent onto one surface of a continuous sheet by ejecting the thermoplastic adhesive agent from the ejecting section, the continuous sheet traveling in a predetermined travel path, the continuous sheet being relevant to an absorbent article, the adhesive agent applying apparatus relevant to an absorbent article comprising:

a contacting-detaching mechanism that causes relative movement between the continuous sheet and the ejecting section along a contacting-detaching direction;
an ejecting mechanism that performs an ejecting operation of the thermoplastic adhesive agent from the ejecting section; and
a controller that controls the contacting-detaching mechanism and the ejecting mechanism,
the controller controlling, in a case where a travel speed of the continuous sheet is greater than a predetermined threshold value, the contacting-detaching mechanism and the ejecting mechanism in such a manner that, while causing the ejecting section to be in a contacting state with the one surface of the continuous sheet, the thermoplastic adhesive agent is ejected from the ejecting section, and
the controller controlling, in a case where the travel speed is less than or equal to the threshold value, the contacting-detaching mechanism and the ejecting mechanism in such a manner that the ejection of the thermoplastic adhesive agent from the ejecting section is stopped and that the continuous sheet and the ejecting section come to a spaced apart state at the time the ejection is stopped or after the ejection has been stopped,
wherein
the contacting-detaching mechanism includes a seesaw member supported in a pivotable manner,
a first roller is provided on one end of the seesaw member,
a second roller is provided on another end of the seesaw member,
the first roller is nearer to the ejecting section than the second roller,
when moving from the contacting state to the spaced apart state the first and second rollers move in opposite directions along the contacting-detaching direction.

2. An adhesive agent applying apparatus relevant to an absorbent article according to claim 1, wherein in a case where the travel speed is less than or equal to the threshold value, the controller controls the contacting-detaching mechanism and the ejecting mechanism in such a manner that ejection of the thermoplastic adhesive agent from the ejecting section is stopped and that the continuous sheet and the ejecting section come to a spaced apart state after the ejection has been stopped.

3. An adhesive agent applying apparatus relevant to an absorbent article according to claim 1, wherein the contacting-detaching mechanism is a mechanism that moves the travel path of the continuous sheet in the contacting-detaching direction.

4. An adhesive agent applying apparatus relevant to an absorbent article according to claim 2, wherein,
the threshold value is a value greater than zero; and
in a case where the travel speed has become less than or equal to the threshold value, the controller controls the ejecting mechanism in such a manner that ejection is stopped before the travel of the continuous sheet is stopped.

5. An adhesive agent applying apparatus relevant to an absorbent article according to claim 4, further comprising:
a heating mechanism that heats the ejecting section,
wherein the continuous sheet is a thermoplastic sheet, and the controller controls the contacting-detaching mechanism in such a manner that, before the travel of the continuous sheet is stopped, the continuous sheet and the ejecting section come to a spaced apart state.

6. An adhesive agent applying apparatus relevant to an absorbent article according to claim 1, wherein the threshold value is set at zero.

7. An adhesive agent applying method of applying a thermoplastic adhesive agent onto one surface of a continuous sheet by ejecting the thermoplastic adhesive agent from an ejecting section, the continuous sheet traveling in a predetermined travel path, the continuous sheet being relevant to an absorbent article, the adhesive agent applying method relevant to an absorbent article comprising:
in a case where a travel speed of the continuous sheet is greater than a predetermined threshold value, ejecting the thermoplastic adhesive agent from the ejecting section while the ejecting section is being in contact with the one surface of the continuous sheet, and
in a case where the travel speed is less than or equal to the threshold value, stopping the ejection of the thermoplastic adhesive agent from the ejecting section and moving the continuous sheet and the ejecting section brom a contacting state in which the ejecting section is in contact with one surface of the continuous sheet to a spaced apart state at the time the ejection is stopped or after the ejection has been stopped,
wherein
a contacting-detaching mechanism is provided which moves with the continuous sheet between the contacting state and the spaced apart state and includes:
a seesaw member supported in a pivotable manner;
a first roller is provided on one end of the seesaw member, and
a second roller is provided on another end of the seesaw member,
wherein the first roller is nearer to the ejecting section than the second roller,
wherein when the contacting-detaching mechanism moves from the contacting state to the spaced apart state the first and second rollers move in opposite directions along a contacting-detaching direction.

* * * * *